United States Patent [19]

Kinast et al.

[11] 4,293,551

[45] Oct. 6, 1981

[54] N-AMINO-3,4,5-TRIHYDROXYPIPERI-DINES, THEIR PRODUCTION AND THEIR MEDICINAL USE

[75] Inventors: Günther Kinast; Lutz Müller; Walter Puls; Rüdiger Sitt, all of Wuppertal, Fed. Rep. of Germany

[73] Assignee: Bayer Aktiengesellschaft, Leverkusen, Fed. Rep. of Germany

[21] Appl. No.: 58,348

[22] Filed: Jul. 17, 1979

[30] Foreign Application Priority Data

Aug. 10, 1978 [DE] Fed. Rep. of Germany ....... 2835069

[51] Int. Cl.³ .................. C07C 211/98; A61K 31/445
[52] U.S. Cl. ..................................... 424/249; 424/251; 424/235; 424/258; 424/263; 424/267; 542/423; 542/424; 544/212; 544/215; 544/264; 544/295; 544/322; 544/333; 544/336; 544/337; 544/407; 546/156; 546/157; 546/162; 546/171; 546/187; 546/193; 546/194; 546/199; 546/208; 546/210; 546/211; 546/214; 546/219; 546/220; 546/243; 546/223; 546/188; 546/242

[58] Field of Search ............... 546/219, 220, 223, 243, 546/242, 208, 214, 156, 157, 162, 171, 199, 193, 194, 210, 211, 188, 187, 207; 424/267, 249, 251, 253, 258, 263; 542/423, 424; 544/337, 407, 336, 212, 215, 322, 333, 295, 264

[56] References Cited

U.S. PATENT DOCUMENTS

| 3,371,093 | 2/1968 | Zenitz et al. | 546/223 |
|---|---|---|---|
| 3,371,094 | 2/1968 | Zenitz et al. | 546/223 |
| 4,137,231 | 1/1979 | Murai et al. | 546/242 |
| 4,145,426 | 3/1979 | Grier et al. | 546/220 |
| 4,146,627 | 3/1979 | Wehinger et al. | 542/424 |
| 4,182,767 | 1/1980 | Murai et al. | 546/242 |

OTHER PUBLICATIONS

Inouye et al. Tetrahedron 23 (1968) pp. 2125-2144.

*Primary Examiner*—Arthur P. Demers
*Attorney, Agent, or Firm*—Sprung, Felfe, Horn, Lynch & Kramer

[57] ABSTRACT

The invention relates to N-amino-3,4,5-trihydroxypiperidines, methods for their production, compositions containing said compounds. Also included are methods for the use of said compounds and compositions.

15 Claims, No Drawings

N-AMINO-3,4,5-TRIHYDROXYPIPERIDINES, THEIR PRODUCTION AND THEIR MEDICINAL USE

The present invention relates to N-amino-3,4,5-trihydroxypiperidines, processes for their production and their use as medicaments acting against diabetes, hyperlipoproteinaemia, adiposity, meteorism, flatulence, gastrointestinal infections, caries and arteriosclerosis, and in animal nutrition for influencing the lean meat/fat ratio in favour of the lean meat proportion.

According to the present invention we provide compounds which are N-amino-3,4,5-trihydroxypiperidines of the general formula

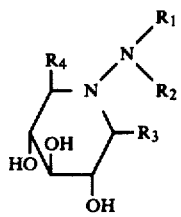

or a salt thereof,
in which $R_1$ denotes a hydrogen atom, a formyl or carboxamido group, or an $R_5$, $COR_5$, $CO_2R_5$, $CONHR_5$, $CONR_5R_6$, $CSR_5$, $CSNH_2$, $CSNHR_5$, $CSNR_5R_6$, $SO_3H$ or $SO_2R_5$ radical, $R_2$ denotes a hydrogen atom or an $R_5$ radical, or $R_1$ and $R_2$ together denote the grouping

$R_3$ denotes a hydrogen atom, a hydroxyl, mercapto, amino, cyano, carboxyl, carboxamido, aminomethyl, sulpho, hydroxymethyl group or an $OR_5$, $SR_5$, $NHR_5$, $NR_5R_6$, $CO_2R_5$, $CONHR_5$, $CONR_5R_6$, $CH_2NHR_5$, $CH_2NR_5R_6$, $CH_2NHR_5$, $CH_2NR_5COR_6$, $CH_2NHSO_2R_5$, $CH_2NR_5SO_2R_6$, $CH_2OR_5$ or $CH_2O\text{-}COR_5$ radical, $R_4$ denotes a hydrogen atom, a hydroxymethyl, formyl, carboxyl or carboxamide group or a $R_5$, $CH_2OR_5$, $CHR_5OH$, $CHR_5OR_6$, $CR_5R_6OH$, $CR_5R_6OR_7$, $CR_5O$, $CO_2R_5$, $CONHR_5$, $CONR_5R_6$ or $CH_2X$ radical, wherein X is halogen, e.g. fluoro, chloro, bromo, $R_5$, $R_6$ and $R_7$ independently of one another denote an optionally substituted, straight-chain, branched or cyclic saturated or unsaturated aliphatic hydrocarbon radical or an optionally substituted aromatic or heterocyclic radical, it also being possible for 2 radicals $R_5$, $R_6$ and $R_7$ to be linked to one another, and $R_8$ and $R_9$ independently of each other denote a hydrogen atom or an $R_5$ radical.

$R_5$, $R_6$ and $R_7$ preferably denote alkyl with 1 to 30, in particular 1 to 18 (especially 1 to 7) carbon atoms, alkenyl or alkinyl with 2 to 18, in particular 3 to 10 (especially 3 to 6) carbon atoms, mono-, bi- or tri-cyclo-alkyl, -alkenyl or -alkadienyl with 3 to 10 carbon atoms, monocyclic or bicyclic carbocyclic aryl with 6 or 10 carbon atoms, or a heterocyclic radical which has 3 to 8, in particular 3 to 6, ring members and which contains 1, 2, 3 or 4 hetero-atoms, in particular N, O or S, and onto which a benzene ring or a further heterocyclic ring of the type mentioned can be fused, it being possible for the radicals mentioned to carry 1 to 5, in particular 1, 2 or 3, substituents.

Examples which may be mentioned of substituents for alkyl are hydroxyl, alkoxy with preferably 1 to 4 carbon atoms, in particular methoxy and ethoxy; alkylcarbonyloxy with up to 7 carbon atoms, benzoyloxy which is optionally substituted by —OH, halogen, in particular F, Cl or Br, $C_1$ to $C_4$ alkyl, $C_1$ to $C_4$ alkoxy, nitro and/or amino, carbonyloxy, heterocyclyl which is derived from a 5-membered or 6-membered heterocyclic compound which contains 1 to 3 hetero-atoms (N, O or S) and can be substituted in the heterocyclic ring by $C_1$ to $C_4$ alkyl, chlorine, bromine or amino, amino, monoalkylamino and dialkylamino with preferably 1 to 4 carbon atoms per alkyl radical, in particular monomethylamino, monoethylamino, dimethylamino and diethylamino, or monoacylamino, the acyl radical being derived from aliphatic (particularly alkane) carboxylic acids with 1 to 7 carbon atoms, aromatic carboxylic acids, in particular phenylcarboxylic acids, which can be substituted in the phenyl radical by —OH, halogen, in particular F, Cl or Br, $C_1$ to $C_4$ alkyl, $C_1$ to $C_4$ alkoxy, nitro and/or amino, or heterocyclic carboxylic acids which are derived from 5-membered or 6-membered heterocyclic compounds which contain 1, 2 or 3 hetero-atoms (N, O or S) and can be substituted in the heterocyclic ring by $C_1$ to $C_4$ alkyl, chlorine, bromine or amino; mercapto, or alkylthio with preferably 1 to 4 carbon atoms, in particular methylthio and ethylthio; halogen, preferably fluorine, chlorine and bromine; alkylcarbonyl with preferably 1 to 4 carbon atoms in the alkyl radical; carboxyl, nitro, cyano, formyl or sulpho; and heterocyclic radicals of the above-mentioned type and radicals of sugars, in particular heterocyclic radicals derived from hexoses or pentoses, which can be linked to the alkyl radical directly via a ring atom or via a —O—, —S— or —NH— bridge.

Examples of the above-mentioned heterocyclic radicals are phthalimido, pyridyl, thienyl, furyl, isoxazolyl, thiazolyl, glucopyranosyl, ribofuranosyl and oxiranyl.

The alkyl radical can also carry a monocyclic, bicyclic or tricyclic (especially aliphatic and particularly alkyl) substituent which preferably has 3 to 10 carbon atoms and can in turn be substituted by hydroxyl, amino, halogen, in particular fluorine, chlorine or bromine, or —COOH.

The alkyl radical preferably carries substituents such as hydroxyl, alkoxy with 1 to 4 carbon atoms, mercapto, alkylthio with 1 to 4 carbon atoms, halogen, nitro, amino, monoalkylamino with 1 to 4 carbon atoms and acylamino, the acyl radical being derived from aliphatic (particularly alkane) carboxylic acids with 1 to 6 carbon atoms.

Possible substituents for the monocyclic, bicyclic or tricyclic radicals $R_1$, $R'$ and $R''$ are those mentioned for the alkyl radicals.

The aryl radicals $R_5$, $R_6$ and $R_7$ can carry one or more, preferably 1, 2 or 3, identical or different substituents Examples of substituents which may be mentioned are: alkyl with 1 to 10 (preferably 1 to 4) carbon atoms, which in turn can be further substituted, for example by chlorine, nitro or cyano; optionally substituted alkenyl radicals with 2 to 10 (preferably 2 to 4) carbon atoms; hydroxyl, or alkoxy with preferably 1 to 4 carbon atoms; amino or monoalkyl- and dialkyl-amino with preferably 1 to 4 carbon atoms per alkyl radical; mercapto, or alkylthio with preferably 1 to 4 carbon atoms; carboxyl, carbalkoxy with preferably 1 to 4 carbon atoms; the sulphonic acid group, alkylsulphonyl with preferably 1 to 4 carbon atoms or arylsulphonyl, preferably phenylsulphonyl; aminosulphonyl or alkylamino- and dialkylamino-sulphonyl with 1 to 4 carbon atoms per alkyl group, preferably methylaminosulphonyl and dimethylaminosulphonyl; nitro, cyano, formyl or alkylcarbonylamino with preferably 1 to 4 carbon atoms; alkylcarbonyl with 1 to 4 carbon atoms, benzoyl, benzylcarbonyl and phenylethylcarbonyl, it being possible for the alkyl, phenyl, benzyl and phenylethyl radicals last-mentioned to be in turn further substituted, for example by chlorine, nitro or hydroxyl. Aryl in this context is preferably phenyl and naphthyl.

The heterocyclic radicals $R_5$, $R_6$ and $R_7$ are preferably derived from hetero-paraffinic, hetero-aromatic or hetero-olefinic 5-membered or 6-membered rings with preferably 1, 2 or 3 identical or different hetero-atoms from the series comprising oxygen, sulphur and nitrogen. These ring systems can carry further substituents, such as hydroxyl, amino or $C_1$ to $C_4$ alkyl groups, or benzene nuclei or further heterocyclic rings, which are preferably 6-membered, of the type mentioned can be fused onto them.

Particularly preferred heterocyclic radicals are derived from furane, pyrane, pyrrolidine, piperidine, pyrazole, imidazole, pyrimidine, pyridazine, pyrazine, triazine, pyrrole, pyridine, benzimidazole, quinoline, isoquinoline and purine.

In preferred compounds within the formula (I), $R_3$ denotes a hydrogen atom or a hydroxyl, sulpho, cyano, aminomethyl, $C_1$ to $C_6$ alkylaminomethyl or ($C_1$ to $C_6$ alkyl)-carbonylaminomethyl group and $R_4$ denotes a hydroxymethyl, hydroxy ($C_1$ to $C_6$ alkyl)-methyl, $C_1$ to $C_7$ alkyl or $C_1$ to $C_5$ alkoxymethyl group.

Very particularly preferred compounds within the formula (I) correspond to the formula

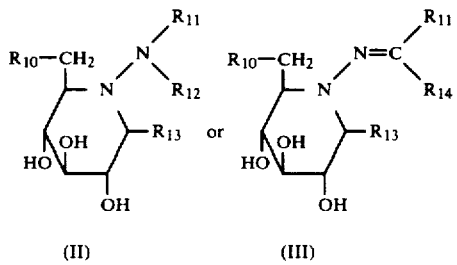

(II)    (III)

in which $R_{10}$ denotes a hydrogen atom or a hydroxyl or methoxy group, $R_{11}$ denotes a hydrogen atom or a $C_1$ to $C_4$ alkyl, $C_1$ to $C_4$ alkoxy, $C_1$ to $C_4$ alkylsulphonyl, $C_1$ to $C_4$ alkylcarbonyl or phenyl group, preferably a hydrogen atom or a methyl, ethyl, acetyl, methylsulphonyl, propionyl or phenyl group, $R_{12}$ denotes a hydrogen atom, a $C_1$ to $C_{12}$ alkyl group which is optionally substituted by hydroxyl, $C_1$ to $C_4$ alkoxy, carboxyl, $C_5$ to $C_7$ cycloalkyl or phenylsulphonylamino, a $C_2$ to $C_4$ alkenyl group, a phenyl, phenyl-$C_1$ to $C_4$ alkyl or benzoylmethyl group which is optionally substituted in the phenyl ring by halogen, $C_1$ to $C_4$ alkyl, hydroxyl, di-$C_1$ to $C_4$ alkylamino or $C_1$ to $C_4$ alkoxy, or a $C_5$ to $C_7$ cycloalkyl, furylmethyl, pyridylmethyl or diphenylmethyl group, $R_{13}$ denotes a hydrogen atom or a ($C_1$ to $C_6$ alkyl)carbonylaminomethyl, phenylcarbonylaminomethyl, phenylsulphonylaminomethyl, ($C_1$ to $C_4$ alkoxy)carbonyl or ($C_1$ to $C_6$ alkyl)-aminocarbonyl group, and $R_{14}$ denotes a hydrogen atom, a $C_1$ to $C_{12}$ alkyl group which is optionally substituted by hydroxyl, $C_1$ to $C_4$ alkoxy or phenylsulphonylamino, a $C_5$ to $C_7$ cycloalkyl, $C_2$ to $C_{12}$ alkenyl or carboxyl group, a phenyl, phenyl-$C_1$ to $C_4$ alkyl or benzoyl group which is optionally substituted by halogen, preferably fluorine or chlorine, $C_1$ to $C_4$ alkyl, hydroxyl, nitro, di-$C_1$ to $C_4$ alkylamino, $C_1$ to $C_4$ alkoxy or carboxyl, or a furyl or pyridyl radical, together with $R_{11}$ and the double-bonded carbon atom, completes a cyclopentane or cyclohexane ring.

According to the present invention there is further provided a process for the production of compounds of formula (I) in which a compound of the general formula

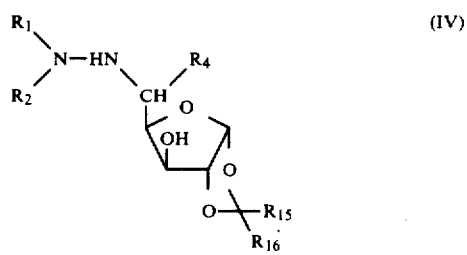

in which $R_{15}$ and $R_{16}$ independently of each other denote a $C_1$ to $C_4$ alkyl group or together denote a $C_4$ to $C_5$ alkylene radical (preferably methyl or together pentamethylene) and $R_1$, $R_2$ and $R_4$ have the above-mentioned meanings, is subjected to acid hydrolysis and the resulting compound of the general formula

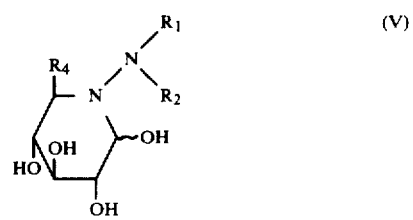

in which $R_1$, $R_2$ and $R_4$ have the above-mentioned meanings, and, if desired, is reacted to give the compounds of the formula (I) $R_3$ has the meanings already given.

Compounds of the formula (I) in which $R_3$ has the meanings already given, with the exception of OH, SH and $NH_2$, and $R_1$, $R_2$ and $R_4$ have the meaning already given are furthermore obtained by a process in which a compound of the general formula

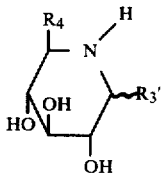

in which $R_4$ has the meaning already given and $R_3'$ has a meaning given for $R_3$, with the exception of hydroxyl, mercapto and amino, is nitrosated, the nitrosation product is reduced and the compound thereby obtained, of the general formula

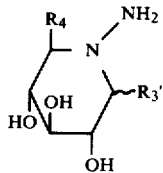

in which $R_3'$ and $R_4$ have the meaning given above, is reacted to give the corresponding compounds of the formula (I) in which $R_1$ and $R_2$ have the meanings given.

The compounds of the formula (VII) can also be obtained from the compounds of the formula (VI) by a process in which the compounds of the formula (VI) are reacted either with hydroxylamine-O-sulphuric acid or with ammonia and chlorine.

Compounds of the formula (I) wherein $R_3$ denotes $OR_5$, SH, $SR_5$, $NH_2$, $NHR_5$, $NR_5R_6$, CN or $SO_3H$ are obtained by a process in which compounds of the formula (V) are reacted with corresponding nucleophiles. The cyano group in compounds of the formula (I) in which $R_3$ is CN can be saponified to the carboxyl group, to the carboxylic acid ester group or to the carboxamide group in the customary manner or reduced to the aminomethyl group in the customary manner and this group can in its turn again be alkylated or acylated. The compounds in which $R_3$=OH can be recovered from the compounds of the formula (I) in which $R_3$ denotes cyano or sulpho by treatment with bases, preferably with alkaline earth metal hydroxides. The compounds of the formula (I) in which $R_3$=hydrogen can be obtained from the compounds of the formula (V) by reducing agents, for example with sodium cyanoborohydride.

Compounds of the general formula

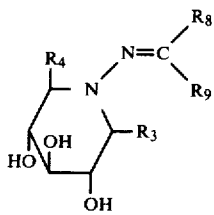

are obtained by a process in which a compound of the formula (VII) is reacted with a corresponding aldehyde or ketone in water or in alcohol, if appropriate in the presence of an acid, in particular acetic acid.

Compounds of the formula (VIII) in which $R_3$ is not OH or SH can be reduced with hydrogen donors, preferably with NaBH$_3$CN in alcohol in the presence of glacial acetic acid or with NaBH$_4$ in alcohol in the presence of glacial acetic acid, to give a compound of the general formula

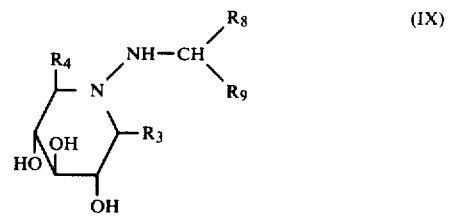

in which $R_3$ has the same meaning as in formula (I) other than OH or SH and $R_4$, $R_8$ and $R_9$ have the above-mentioned meanings.

The compounds of the formula (IX) in which $R_3$ is not OH or SH can be reacted with aldehydes and ketones and NaBH$_3$CN in alcohol in the presence of acid, for example, glacial acetic acid, to give compounds of the formula (I) wherein $R_3$ is not OH or SH, $R_4$ has the meaning indicated and $R_1$ and $R_2$ independently of one another represent

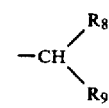

in which $R_8$ and $R_9$ have the above-mentioned meanings.

Furthermore, the compounds of the formula (IX) and the compounds of the formula (VII) can be reacted with carboxylic acid chlorides and anhydrides and with sulphonic acid chlorides, in particular in water or alcohol/water mixtures in the presence of a base, such as NaOH, K$_2$CO$_3$ or NaHCO$_3$, but in particular in the presence of a basic ion exchanger, to give compounds of the general formula

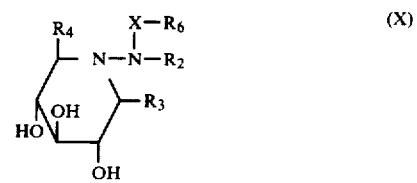

in which

X denotes CO or SO$_2$ and $R_2$, $R_3$, $R_4$ and $R_6$ have the above-mentioned meanings.

Compounds of the formula (X) can be reduced, for example with NaBH$_4$ in trifluoroacetic acid, to give compounds of the formula (I) wherein $R_1$ represents —CH$_2$—R$_6$ and $R_2$, $R_3$, $R_4$ and $R_6$ have the meaning indicated.

Compounds of the formula (I) wherein $R_1$ denotes an optionally substituted 2-hydroxyalkyl group or an optionally substituted 2-cyanoalkyl group, in particular the 2-hydroxyethyl group and the 2-cyanoethyl group, and $R_2$, $R_3$, $R_4$, $R_8$ and $R_9$ have the meanings indicated, can be obtained from the compounds of the formulae (VII) and (IX) by reaction with epoxides and α,β-unsaturated carbonyl compounds, such as acrylonitrile.

Compounds of the general formula

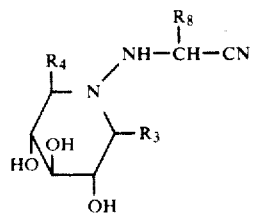
(XI)

in which

R$_3$, R$_4$ and R$_8$ have the above-mentioned meanings, are obtained by a process in which compounds of the formula (VII) are reacted with 2-hydroxynitriles of the formula (XII)

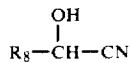
(XII)

in which R$_8$ has the above-mentioned meaning, or by a process in which compounds of the formula (VIII) in which R$_8$ has the above-mentioned meaning and R$_9$ denotes a hydrogen atom are reacted with hydrocyanic acid.

Compounds of the formulae (IX) and (VII) wherein R$_3$ and R$_3'$ denote a cyano group which is to be reduced to the aminomethyl group are appropriately protected, before the reduction, by reaction with carboxylic acid chlorides or carboxylic acid anhydrides, in particular by reaction with chloroformic acid C$_1$–C$_4$-alkyl esters. After the hydrogenation, or if appropriate after a further reaction, the protective group can easily be split off under acid or basic conditions.

Acid hydrolysis of compounds of the formula (IV) to give compounds of the formula (V) is appropriately carried out in a manner such that the products are trapped in the form of adducts of sulphurous acid (R$_3$=SO$_3$H) and the compounds of the formula (I) (R$_3$=OH) are liberated from these bisulphite addition products, as already mentioned, by treatment with bases, preferably alkaline earth metal hydroxides, such as Ca(OH)$_2$, SR(OH)$_2$ or, in particular, Ba(OH)$_2$.

The production of compounds of the formula (IV) is illustrated as shown in the reaction scheme which follows, the starting compounds for both reaction routes being known from the literature.

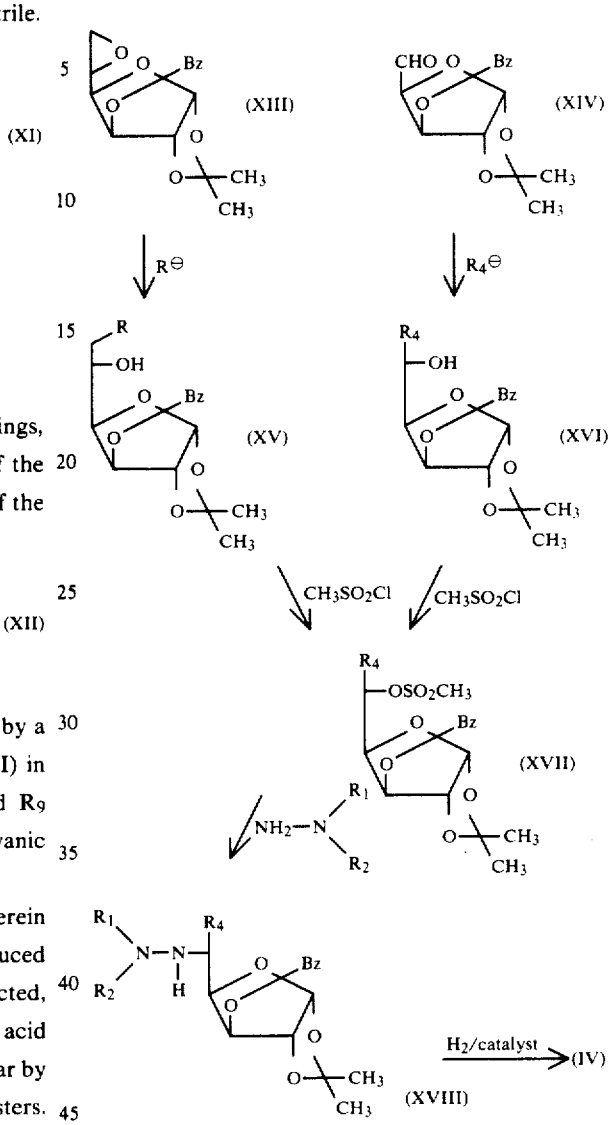

In the above reaction scheme the group —CH$_2$—R denotes R$_4$. R$_1$, R$_2$ and R$_4$ have the above-mentioned meanings and Bz represents a benzyl group, in particular a 4-nitrobenzyl group.

The reactant "R$_4^\ominus$" is employed, for example, as R$_4$MgHal, R$_4$Li, LiAlH$_4$ or H$_2$/catalyst and "R$^\ominus$" is employed, for example, as an alcoholate.

The intermediate products (XV) and (XVI) are ido-compounds. The gluco-isomers of (XVI) likewise formed must be separated off if necessary. However, it is also possible to follow a procedure in which ido-compounds and gluco-compounds or mixtures of the two are oxidised, for example with chromium trioxide, to give the ketones of the general formula

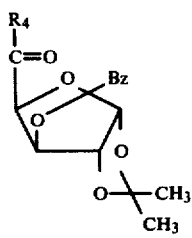

these ketones or the aldehyde (XIV) (R$_4$=H) are reacted with the hydrazines of the formula

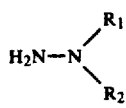

the hydrazones thereby formed are reduced, for example with NaBH$_4$ or with NaCNBH$_3$ in alcohol/glacial acetic acid, and the gluco-isomers are separated from the ido-isomers by chromatography. The aldehyde hydrazones can be reacted, as already described above, with organometallic compounds R$_4$MgBr or R$_4$Li to give an ido/gluco mixture of the formula (XVIII), from which, if desired, the gluco-isomer is separated off by chromatography.

The preparation of N-phenylamino-1-desoxynojirimicin may be described, by way of example, in the following text. The starting compound (XX) used in this preparation is known from the literature.

with the aid of a basic ion exchanger. The compounds of the formula (I) in which R$_3$-OH are then appropriately isolated by removing the solvent under gentle conditions, for example by lyophilisation.

A preferred embodiment of splitting the isopropylidene protective group off from compounds of the formula (IV) and (XXII) consists in saturating an aqueous or watercontaining alcoholic solution of the compounds of the formula (IV) and (XXII) with SO$_2$ and storing the solution at temperatures between 20° and 80° C. for several days. The compounds of the formula (I) are then obtained as bisulphite adducts (R$_3$=—SO$_3$H), which in most cases crystallise well, from which the compounds of the formula (I) (R$_3$=OH) can be liberated with the aid of, for example, aqueous Ba(OH)$_2$.

The reduction of compounds of the formula (I) in which R$_3$=OH to give compounds of the formula (I) in which R$_3$=H may be carried out using alkali metal borohydrides, alkali metal cyanoborohydrides or dialkylaminoboranes. It is preferable to use sodium cyanoborohydride in the presence of glacial acetic acid in an aqueous solution or in a water-miscible water-containing organic solvent, such as, for example, dioxane, at room temperature or, if appropriate, at elevated temperature. However, the reduction is very particularly preferably carried out catalytically with Pt or Pd as the catalyst, or in the presence of Raney nickel. In this case, the reaction is preferably carried out in an aqueous solution at room temperature.

The carbonyl compounds for the reactions of (I) in which R$_1$ and R$_2$=H to give (VIII) and of (IX) to give compounds of the formula (I) wherein R$_1$ and R$_2$ denote

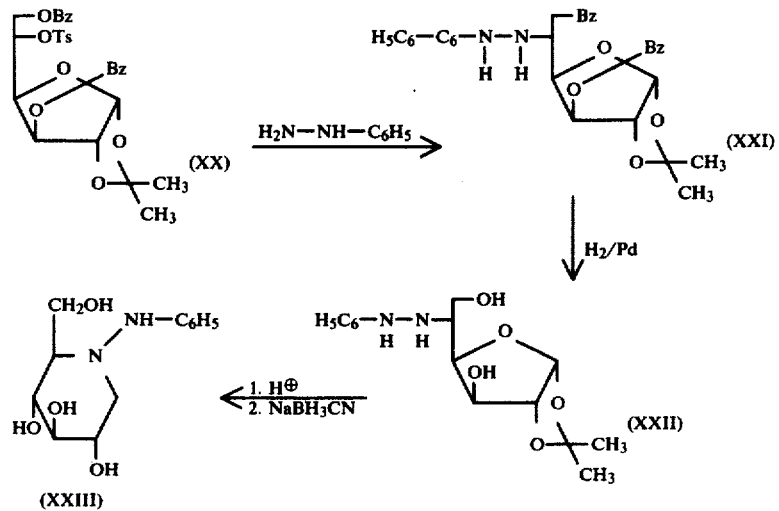

Splitting the isopropylidene protective group off from the compounds of the formula (IV) and (XXII) is carried out in a moderately strongly acid to weakly acid solution, preferably in a pH range between 1 and 4, in an aqueous solution or in a water-miscible, water-containing organic solvent. Acids which can be used are dilute mineral acids, such as, for example, sulphuric acids, hydrochloric acid or nitric acid, or organic acids, such as alkane carboxylic acids, e.g. acetic acid. The reaction is preferably carried out under atmospheric pressure and at a temperature between room temperature and the boiling point of the solvent.

For working up of the reaction mixture, the acid is neutralised and is separated off in the form of the salt or

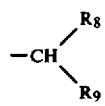

are either known, or they can be prepared by standard processes.

Typical examples which may be mentioned specifically are: straight-chain or branched alkylaldehydes, such as formaldehyde, acetaldehyde, n-propanal, n-butanal, 2-methylpropanal, n-pentanal, 2-methylbutanal, 3-methylbutanal, 2,2-dimethylpropanal, n-hexanal, 2-ethylbutanal, n-heptanal and n-octanal; alkenylaldehydes, such as propenal, 2-methylpropenal, 2-butenal, 2-methyl-2-butenal and 2-ethyl-2-hexanal; cyclic aldehydes, such as cyclopropanecarbaldehyde, cyclopentanecarbaldehyde, cyclopentaneacetaldehyde and cyclohexanecarbaldehyde; benzaldehyde, o-, m- and p-toluenecarbaldehydes and phenylacetaldehydes; straightchain and branched alkylaldehydes which are substituted by hydroxyl, such as 5-hydroxypentanal, 2-hydroxy-3-methylbutanal, 2-hydroxy-2-methylpropanal, 4-hydroxybutanal, 2-hydroxypropanal and 8-hydroxyoctanal; straight-chain and branched alkylaldehydes which are substituted by amino, such as 5-aminopentanal, 2-aminopropanal, 3-aminopropanal, 4-aminobutanal, 2-amino-3-methylbutanal and 8-aminooctanal, and mono-N-alkyl derivatives thereof; and straight-chain and branched alkylaldehydes which are disubstituted by amino and hydroxyl, such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal and 2-amino-3-hydroxyoctanal and mono-N-alkyl derivatives thereof.

Further examples are: methoxy-acetaldehyde, ethoxy-acetaldehyde, n-propoxy-acetaldehyde, i-propoxyacetaldehyde, n-butoxy-acetaldehyde, i-butoxy-acetaldehyde, tert.butoxy-acetaldehyde, cyclopropylmethoxy-acetaldehyde, cyclopropoxyacetaldehyde, 2-methoxy-ethoxy-acetaldehyde, 2-ethoxy-ethoxy-acetaldehyde, 2-methoxy(1-methyl-ethoxy)-acetaldehyde, 2-ethoxy(1-methyl-ethoxy)-acetaldehyde, phenoxyacetaldehyde, 2-methoxy-2-methyl-acetaldehyde, 2-ethoxy-2-methyl-acetaldehyde, 2-n-propoxy-2-methyl-acetaldehyde, 2-(i-propoxy)-2-methyl-acetaldehyde, 2-(n-butoxy)-2-methyl-acetaldehyde, 2-(i-butoxy)-2-methyl-acetaldehyde, 2-(tert.-butoxy)-2-methyl-acetaldehyde, 2-cyclopropylmethoxy-2-methyl-acetaldehyde, 2-cyclopropoxy-2-methylacetaldehyde, 2-methoxy-ethoxy-α-methyl-acetaldehyde, 2-ethoxy-ethoxy-α-methylacetaldehyde, 2-methoxy-(1-methylethoxy)-α-methyl-acetaldehyde, 2-methoxy-2,2-dimethylacetaldehyde, 2-ethoxy-2,2-dimethyl-acetaldehyde, 2-cyclopropylmethoxy-acetaldehyde, 2-ω-butoxy-2,2-dimethyl-acetaldehyde, methylthio-acetaldehyde, ethylthio-acetaldehyde, n-propylthio-acetaldehyde, i-propylthio-acetaldehyde, cyclopropyl-methylthio-acetaldehyde, 3-methoxy-propanal, 3-ethoxy-propanal, 3-n- and 3-i-propoxy-propanal, 3-n-, 3-i- and 3-tert.-butoxy-propanal, 3-cyclopropoxy-propanal, 3-cyclopropylmethoxy-propanal, 3-methoxy-3-methyl-propanal, 3-ethoxy-3-methyl-propanal, 3-n- and 3-i-propoxy-3-methylpropanal, 3-n-, 3-i- and 3-tert.-butoxy-3-methyl-propanal, 2,3- and 4-methoxy-butanal, 2,3- and 4-ethoxy-butanal, 2-methylthio-propanal, 2-ethylthio-propanal, 3-methylthiopropanal, 3-ethylthio-propanal, 2-methylthio-butanal, 3-methylthio-butanal, 4-methylthio-butanal, furfurol, tetrahydrofurfurol, thiophene-2-aldehyde, 5-bromothiophene-2-aldehyde, 5-methyl-furfurol and pyram-carbaldehyde.

In addition, examples of ketones which may be mentioned are: acetone, methyl ethyl ketone, methyl n-propyl ketone, diethyl ketone, methyl butyl ketone, cyclopentanone, di-n-propyl ketone, cyclohexanone, 3-methylcyclohexanone, 4-methylcyclohexanone, acetophenone, propiophenone, butyrophenone, phenylacetone, p-methoxyacetophenone and m-nitroacetophenone.

Formic acid, for example, can be used as the hydrogen donor reducing agent for the reductive alkylation reactions (Leuckart-Wallach reaction). The formic acid is used in a large excess. The reaction can be carried out in an aqueous solution if formaldehyde is used as the carbonyl component and in anhydrous formic acid if ketones and less reactive aldehydes are used. The reaction temperatures are between 100° and 200° C., and if appropriate the reaction must be carried out in an autoclave.

Alkali metal cyanoborohydrides, dialkylaminoboranes and alkali metal borohydrides are used as hydrogen donor reducing agents both for the reductive alkylation and for the reduction of the hydrazones, for example (VIII). In this process variant, it is particularly preferable to use sodium cyanoborohydride.

In general, the reaction is carried out at room temperature. However, it can also be favourable to heat the mixture to the reflux temperature.

The process is usually carried out in an inert solvent. Although anhydrous aprotic solvents can be employed (for example tetrahydrofurane if the reducing agent is a dialkylaminoboranes, such as dimethylaminoborane), a protic solvent is usually used. A particularly suitable protic solvent is a lower alkanol. However, it is also possible to use water or an aqueous lower alkanol (for example aqueous methanol or ethanol) or other aqueous solvent systems, such as, for example, aqueous dimethylformamide, aqueous hexamethylphosphoric acid triamide, aqueous tetrahydrofurane or aqueous ethylene glycol dimethyl ether.

The process is usually carried out in a pH range of 1 to 11, and a pH range of between 4 and 7 is preferred.

The following active compounds may be listed as preferred examples of compounds according to the invention:

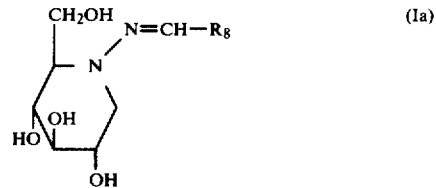

in which $R_8$ denotes a hydrogen atom or a methyl, ethyl, isopropyl, n-hexyl, n-undecyl, cyclopentyl, hydroxymethyl, methoxymethyl, 2-phenylsulphonylaminoethyl, vinyl, carboxyl, phenyl, benzyl, 4-chlorophenyl, 3-fluorophenyl, 2-methylphenyl, 4-hydroxyphenyl, 4-dimethylaminophenyl, 2-nitrophenyl, benzoyl, 3-methoxyphenyl, 2-carboxyphenyl, fur-2-yl or pyrid-3-yl group or a radical of the formula

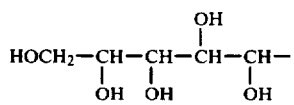

Preferred compounds according to the invention are furthermore those of the formula

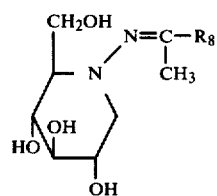 (Ib)

in which

R₈ denotes a methyl, phenyl or 2-phenylethyl group.

Preferred compounds according to the invention also include the compounds of the formulae

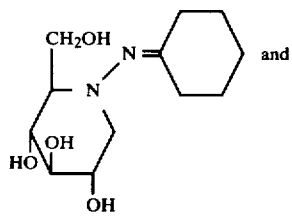 (Ic)

and

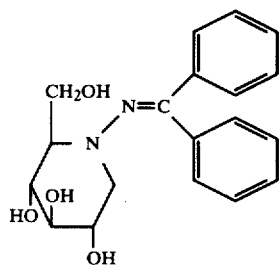 (Id)

Further preferred compounds according to the invention correspond to the general formula

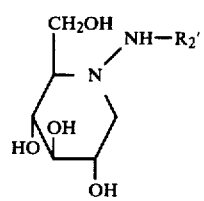 (XXIV)

in which

R₂' denotes a hydrogen atom or a methyl, ethyl, n-propyl, isobutyl, n-heptyl, n-dodecyl, cyclopentylmethyl, 2-hydroxyethyl, 2-methoxyethyl, 3-phenylsulphonylaminopropyl, allyl, carboxymethyl, benzyl, 2-phenylethyl, 4-chlorobenzyl, 3-fluorobenzyl, 2-methylbenzyl, 4-hydroxybenzyl, 4-dimethylaminobenzyl, phenyl, phenylcarbonylmethyl, 3-methoxybenzyl, 2-carboxybenzyl, fur-2-ylmethyl, pyrid-3-ylmethyl, isopropyl, cyclohexyl, 1-phenylethyl, diphenylmethyl or 1-methyl-3-phenylpropyl group or a radical of the formula

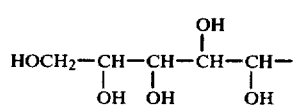

Further preferred compounds according to the invention correspond to the general formula

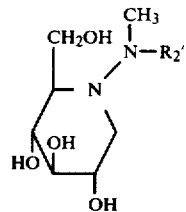 (XXV)

in which

R₂' has the meaning given above.

Further preferred compounds according to the invention correspond to the general formula

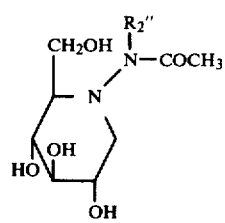 (XXVI)

in which

R₂" denotes a hydrogen atom or a methyl, ethyl, isobutyl, n-heptyl, 2-hydroxyethyl, allyl, carboxymethyl, benzyl, 2-phenethyl, 4-chlorobenzyl, 2-methylbenzyl, 4-hydroxybenzyl, phenyl, fur-2-ylmethyl, pyrid-3-ylmethyl, isopropyl, cyclohexyl or 1-phenylethyl group.

Further preferred compounds according to the invention correspond to the general formula

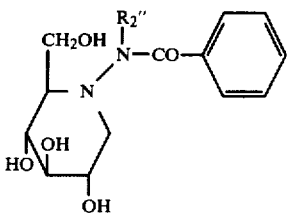 (XXVII)

in which

R₂" has the meaning given above.

Further preferred compounds according to the invention correspond to the general formula

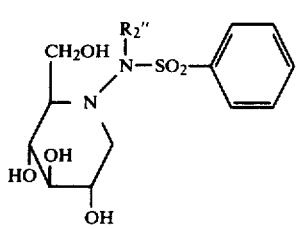 (XXVIII)

in which

R₂" has the meaning given above.

Further preferred compounds according to the invention correspond to the general formula

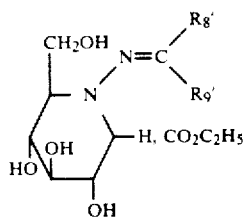  (XXIX)

in which

R$_8'$ denotes a hydrogen atom,

R$_9'$ denotes a hydrogen atom or a methyl, isopropyl, n-hexyl, hydroxymethyl, vinyl, carboxyl, phenyl, benzyl, 4-chlorophenyl, 2-methylphenyl, 4-hydroxyphenyl, 3-methoxyphenyl, fur-2-yl or pyrid-3-yl group, or R$_8'$ denotes a methyl group and R$_9'$ denotes a methyl or phenyl group, or R$_8'$ and R$_9'$, together with the carbon atom, complete a cyclohexane ring.

Further preferred compounds according to the invention correspond to the general formulae

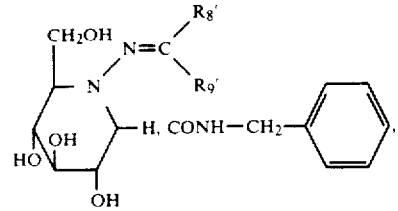  (XXX)

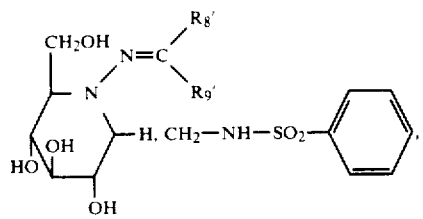  (XXXI)

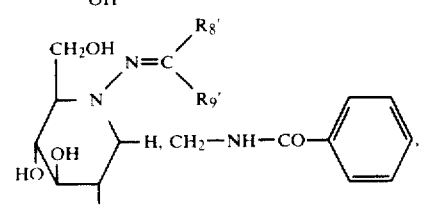  (XXXII)

and

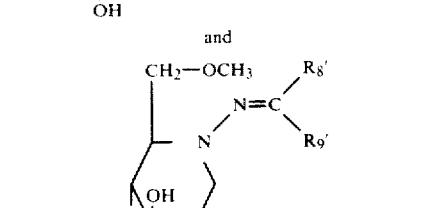  (XXXIII)

In formulae (XXX) to (XXXIII), R$_8'$ and R$_9'$ have the meanings given above.

Further preferred compounds according to the invention correspond to the general formulae

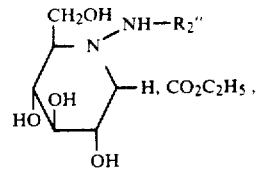  (XXXIV)

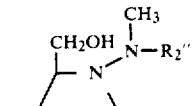  (XXXV)

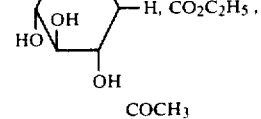  (XXXVI)

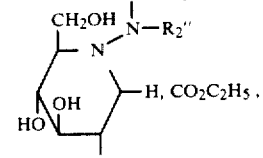  (XXXVII)

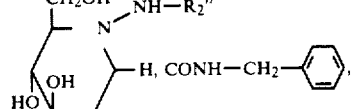  (XXXVIII)

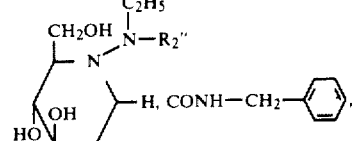  (XXXIX)

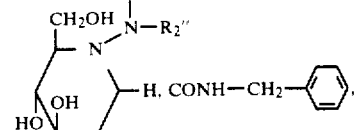  (XL)

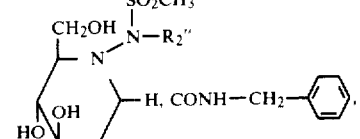  (XLI)

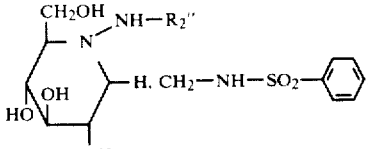  (XLII)

-continued

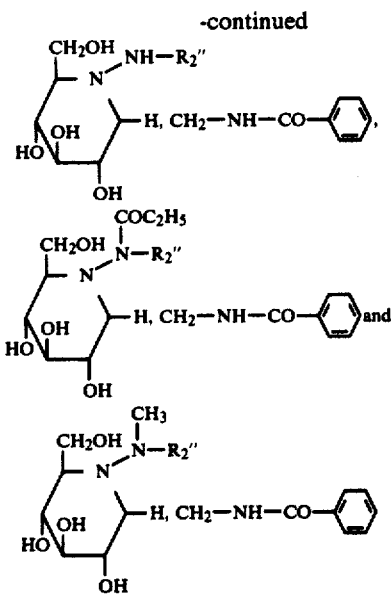

In formulae (XXXIV) to (XLV), R₂″ has the meaning given above.

Further preferred compounds according to the invention correspond to the formula

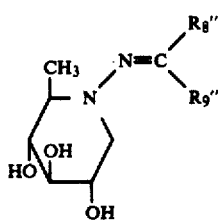

in which

R₈″ denotes a hydrogen atom, and

R₉″ denotes a hydrogen or a methyl, ethyl, isopropyl, n-heptyl, n-undecyl, n-cyclopentyl, hydroxymethyl, methoxymethyl, 2-phenylsulphonylaminoethyl, vinyl, carboxyl, phenyl, benzyl, 4-chlorophenyl, 3-fluorophenyl, 2-methylphenyl, 4-hydroxyphenyl, 4-dimethylaminophenyl, 2-nitrophenyl, benzoyl, 3-methoxyphenyl, 2-carboxyphenyl, fur-2-yl or pyrid-3-yl group, or R₈″ denotes a methyl group and R₉″ denotes a methyl, phenyl or 2-phenethyl group, or R₈″ and R₉″ denote phenyl groups; or R₈″ and R₉″, together with the carbon atom, complete a cyclohexane ring;

or

R₈″ denotes a hydrogen atom and

R₉″ denotes a radical of the formula

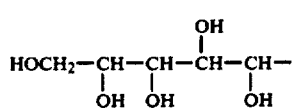

Further preferred compounds according to the invention correspond to the general formula

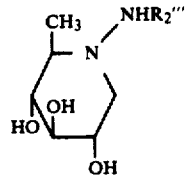

in which

R₂‴ denotes a hydrogen atom or a methyl, ethyl, n-propyl, isobutyl, n-heptyl, n-dodecyl, cyclopentylmethyl, 2-hydroxyethyl, 2-methoxyethyl, 3-phenylsulphonylaminopropyl, allyl, carboxymethyl, benzyl, 2-phenylethyl, 4-chlorobenzyl, 3-fluorobenzyl, 2-methylbenzyl, 4-hydroxybenzyl, 4-dimethylaminobenzyl, phenyl, phenylcarbonylmethyl, 3-methoxybenzyl, 2-carboxybenzyl, fur-2-ylmethyl, pyrid-3-methyl, isopropyl, cyclohexyl, 1-phenylethyl, diphenylmethyl or 1-methyl-3-phenylpropyl group or a radical of the formula

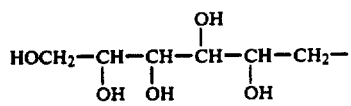

Further preferred compounds according to the invention correspond to the general formula

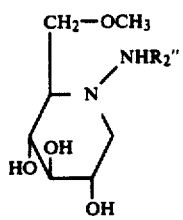

in which R₂″ has the meaning given above.

The compounds according to the invention are inhibitors of the α-glucosidases of the gastrointestinal tract. They can thus inhibit the digestion of carbohydrates. In addition, they inhibit the absorption of cholesterol and triglycerides from the intestines. They are therefore suitable as therapeutic agents for: prediabetes, gastritis, constipation, meteorism, flatulence, gastrointestinal infections, hypertension, caries, arteriosclerosis and, in particular, adiposity, diabetes and hyperlipoproteinaemia.

To broaden the action spectrum, it can be advisable to combine inhibitors for glycoside hydrolases which complement one another in their action, the combination being either combinations of the inhibitors according to the invention with one another or combinations of the inhibitors according to the invention with inhibitors which are already known. Thus, for example, it can be appropriate to combine saccharase inhibitors according to the invention with amylase inhibitors which are already known.

In some cases, combinations of the inhibitors according to the invention with known oral antidiabetic agents (β-cytotropic sulphonylurea derivatives and/or biguanides having an action on the blood sugar), with active compounds which lower the blood lipid level, such as, for example, clofibrate, nicotinic acid and cholestyramine, with bactericidal therapeutic agents and with antihypertensive agents are also advantageous.

The compounds can be administered without dilution, for example as powders or in a gelatine casing, or in combination with an excipient in a pharmaceutical composition.

Pharmaceutical formulations can contain a relatively large or relatively small amount of the active compound, for example 0.1% to 99.5%, in combination with a pharmaceutically acceptable non-toxic, inert excipient, it being possible for the excipient to contain one or more solid, semi-solid or liquid diluents, fillers and/or a non-toxic, inert and pharmaceutically acceptable formulation auxiliary.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention also provides a medicament in dosage unit form comprising a compound of the invention.

The invention also provides a medicament in the form of tablets (including lozenges and granules), dragees, capsules, pills or ampoules comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in animals, which comprises administering to the animals a compound of the invention alone or in admixture with a diluent or in the form of a medicament according to the invention.

It is envisaged that these active compounds will preferably be administered perorally. Preferred pharmaceutical compositions and medicaments are therefore those adapted for administration such as oral administration. Administration in the method of the invention is preferably oral administration.

As stated above, other therapeutic agents can also be taken. Although the dosage and the dosage scheme should be carefully balanced in each case, applying well-founded professional judgement and taking into account the age, the weight and the condition of the patient and the nature and severity of the disease, the dosage will usually be in a range between about 0.1 and about 50 mg saccharase inhibitor/kg of the body weight per day. In some cases an adequate therapeutic effect will be achieved with a relatively small dose, whereas in other cases a larger dose will be required.

Oral administration can be carried out using solid and liquid dosage units, such as, for example, powders, tablets, dragees, capsules, granules, suspensions, solutions and the like.

A powder is prepared by comminuting the substance to a suitable size and mixing it with a pharmaceutical excipient, which is likewise comminuted. Although an edible carbohydrate, such as, for example, starch, lactose, sucrose or glucose is usually used for this purpose and can also be used in this case, it is desirable to use a carbohydrate which cannot be metabolised, such as, for example, a cellulose derivative.

Sweeteners, flavouring additives, preservatives, dispersing agents and colouring agents can also be co-used.

The capsules can be produced by preparing the powder mixture described above and by filling gelatine casings which have already been formed. Before the filling operation, lubricants, such as, for example, silica gel, talc, magnesium stearate, calcium stearate or solid polyethylene glycol, can be added to the powder mixture. A disintegrator or solubilising agent, such as, for example, agar-agar, calcium carbonate or sodium carbonate, can likewise be added to the mixture in order to improve the accessibility of the inhibitor when the capsule is taken.

Tablets are produced, for example, by preparing a powder mixture, of coarse or fine grain size, and adding a lubricant and disintegrator, Tablets are formed from this mixture. A powder mixture is prepared by mixing the substance, which has been comminuted in a suitable manner, and making up with a diluent or another excipient, as described above. Further substances which are added if appropriate are a binder: for example carboxymethylcellulose, alginates, gelatine or polyvinylpyrrolidones, a solution retarder, such as, for example, paraffin, a resorption accelerator, such as, for example, a quaternary salt, and/or an adsorbent, such as, for example, bentonite, kaolin or dicalcium phosphate. The powder mixture can be granulated, together with a binder, such as, for example, syrup, starch paste or acacia mucillage, or solutions of cellulose materials or polymeric materials. The product is then pressed through a coarse sieve. As an alternative to this, the powder mixture can be allowed to run through a tabletting machine and the resulting pieces of non-uniform shape can be comminuted down to a particle size. A lubricant, such as, for example, stearic acid, a stearate salt, talc or mineral oil, can be added to the resulting particles so that these do not stick in the tablet-forming nozzles. This mixture, which has been given slip properties, is then pressed into tablet form. The active compounds can also be combined with free-flowing inert excipients and brought direct into tablet form omitting the granulating or fragmentation steps. The product can be provided with a clear or opaque protective shell, for example a coating of shellac, a coating of sugar or polymeric substances and a polished shell of wax. Dyestuffs can be added to these coatings so that the different dosage units can be differentiated.

The formulation forms to be administered orally, such as, for example, solutions, syrups and elixirs, can be prepared in dosage units, so that a specific amount of the formulation contains a specific amount of active compound. A syrup can be prepared by dissolving the active compound in an aqueous solution which contains suitable flavouring agents; elixirs are obtained using non-toxic, alcoholic excipients. Suspensions can be prepared by dispersing the compound in a non-toxic excipient. Solubilising agents and emulsifying agents, such as, for example, ethoxylated isostearyl alcohols and polyoxyethylenesorbitol esters, preservatives, flavour-improving additives, such as, for example, peppermint oil or saccharin, and the like, can also be added.

Dosage instructions can be indicated on the capsule. In addition, it is possible to safeguard the dosage by releasing the active compound in a delayed manner, for example by enclosing the active compound in polymer substances, waxes or the like.

In addition to the above-mentioned pharmaceutical compositions, foodstuffs containing these active compounds can also be prepared, for example sugar, bread, potato products, fruit juice, beer, chocolate and other confectionery, and preserves, such as, for example, jam, and in this case a therapeutically effective amount of at least one of the inhibitors according to the invention is added to these products.

The foodstuffs produced using the active compounds according to the invention are suitable both for the diet of subjects suffering from metabolism disorders and for the nutrition of healthy persons in the sense of a diet which prevents metabolism disorders.

The inhibitors according to the invention furthermore have the property of influencing to a great extent the relationship between the proportion of undesired fat to the proportion of desired meat of low fat content (lean meat) in animals in favour of the lean meat. This is of particular importance for rearing and keeping agricultural livestock, for example in the fattening of pigs, but is also of considerable importance for rearing and keeping other livestock and pets. Using the inhibitors can furthermore lead to a considerable rationalisation of feeding of animals, from the point of view of time, quantity and quality. Since the inhibitors cause a certain delay in digestion, the residence time of the nutrients in the digestive tract is extended and this makes possible ad libitum feeding, which is associated with a low expenditure. Moreover, using the inhibitors according to the invention in many cases results in a considerable saving of valuable protein feed.

The active compounds can thus be used in virtually all fields of animal nutrition as agents for reducing the deposition of fat and for saving feed protein.

The activity of the active compounds is largely independent of the species and sex of the animals. The active compounds prove particularly valuable in the case of species of animals which, generally or at certain periods of their life, tend to deposit relatively large amounts of fat.

The following livestock and pets may be mentioned as examples of animals for which the inhibitors can be employed for reducing the deposition of fat and/or for saving feed protein: warm-blooded animals, such as cattle, pigs, horses, sheep, goats, cats, dogs, rabbits, fur-bearing animals, for example mink and chinchillas, other pets, for example guineapigs and hamsters, laboratory animals and zoo animals, for example rats, mice, apes and the like, and poultry, for example broilers, hens, geese, ducks, turkeys, pigeons, parrots and canaries, and cold-blooded animals, such as fish, for example carp, and reptiles, for example snakes.

Because of the favourable properties of the active compounds, the amount of the active compounds which is administered to the animals to achieve the desired effect can be varied substantially. It is preferably about 0.5 mg to 2.5 g and in particular 10 to 100 mg/kg of feed per day. The period of administration can be from a few hours or days up to several years. The appropriate amount of active compound and the appropriate period of administration are closely related to the aim of feeding. They depend, in particular, on the species, age, sex, state of health and nature of keeping of the animals and can easily be determined by any expert.

The active compounds according to the invention are administered to the animals by the customary methods. The nature of the administration depends, in particular, on the species, the behaviour and the general condition of the animals. Thus, administration can be effected orally once or several times daily at regular or irregular intervals. For reasons of expediency, in most cases oral administration, in particular in the rhythm of the intake of food and/or drink by the animals, is to be preferred.

The active compounds can be administered as pure substances or in the formulated form, the formulated form being understood as a premix, that is to say as a mixture with non-toxic inert carriers of any desired nature, as a part of a total ration in the form of a supplementary feed or as a mixing component of a mixed feed for use by itself. Administration of suitable formulations via the drinking water is also included.

The active compounds, optionally in the formulated form, can also be administered in a suitable form together with other nutrients and active compounds, for example mineral salts, trace elements, vitamins, proteins, energy carriers (for example starch, sugars, fats), dyestuffs and/or flavouring agents or other feed additives, such as, for example, growth promoters. The active compounds can be administered to the animals before, during or after intake of the feed.

Oral administration together with the feed and/or drinking water is recommended, the active compounds being added to all or parts of the feed and/or drinking water as required.

The active compounds can be admixed to the feed and/or drinking water in accordance with customary methods by simple mixing as pure substances, preferably in the finely divided form or in the formulated form mixed with edible, non-toxic carriers, and optionally also in the form of a premix or a feed concentrate.

The feed and/or drinking water can contain the active compounds according to the invention in a concentration of, for example, about 0.001 to 5.0%, in particlar 0.02 to 2.0% (by weight). The optimum level of the concentration of the active compound in the feed and/or drinking water depends, in particular, on the amount of feed and/or drinking water taken in by the animals and can easily be determined by any expert.

The invention thus provides a medicated feed, comprising a compound of the present invention and a nutrition material.

The nature of the feed and its composition is irrelevant in this context. All the customary commercially available or specific feed compositions, which preferably contain the customary equilibrium of energy substances and proteins, including vitamins and mineral substances, necessary for balanced nutrition, can be used. The feed can be composed, for example, of vegetable substances, for example shredded oilcake, shredded cereal and cereal byproducts, and also hay, silage fodder, beet and other forage plants, of animal substances, for example meat products and fish products, bone meal, fats, vitamins, for example A, D, E, K and B complex, and specific sources of protein, for example yeasts, and certain aminoacids and mineral substances and trace elements, such as, for example, phosphorus and iron, zinc, manganese, copper, cobalt, iodine and the like.

Premixes can preferably contain about 0.1 to 50%, in particular 0.5 to 5.0% (by weight) of, for example, N-amino-1-desoxynojirimicin, in addition to any desired edible carriers and/or mineral salts, for example carbonated feed lime, and are prepared by the customary mixing methods.

Mixed feeds preferably contain 0.001 to 5.0%, in particular 0.02 to 2.0% (by weight) of, for example, N-amino-1-desoxynojirimicin, in addition to the customary raw material components of a mixed feed, for example shredded cereal or cereal by-products, shredded oilcake, animal protein, minerals, trace elements and vitamins. They can be prepared by the customary mixing methods.

In premixes and mixed feedstuffs, preferably, the active compounds can also optionally be protected from air, light and/or moisture by suitable agents which coat their surface, for example with non-toxic waxes or gelatine.

The following is an example of the composition of a finished mixed feed for poultry, which contains an active compound according to the invention: 200 g of wheat, 340 g of maize, 360.3 g of coarse soya bean meal, 60 g of beef tallow, 15 g of dicalcium phosphate, 10 g of calcium carbonate, 4 g of iodonated sodium chloride, 7.5 g of a vitamin/mineral mixture and 3.2 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$. The active compound premix contains, for example, N-amino-1-desoxynojirimicin in the desired amount, for example 1,600 mg, and in addition 1 g of DL-methionine as well as an amount of soya bean meal such that 3.2 g of premix are formed.

The following is an example of the composition of a mixed feed for pigs, which contains an active compound of the formula (I): 630 g of shredded cereal feed (composed of 200 g of shredded maize, 150 g of shredded barley, 150 g of shredded oats and 130 g of shredded wheat), 80 g of fish meal, 60 g of coarse soya bean meal, 58.8 g of tapioca meal, 38 g of brewer's yeast, 50 g of a vitamin/mineral mixture for pigs (composition, for example, as for the chick feed), 30 g of linseed cake meal, 30 g of maize gluten feed, 10 g of soya bean oil, 10 g of sugarcane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or a similar composition, for rearing and fattening other animals.

The inhibitors can be used individually or in any desired mixtures with one another.

In vitro saccharase inhibition test

The in vitro saccharase inhibition test makes it possible to determine the inhibitory activity of the substances according to the invention on enzymes by comparing the activity of solubilised intestinal disaccharidase complex in the presence and in the absence (so-called 100% value) of the inhibitor. A virtually glucose-free sucrose (glucose < 100 ppm) is used as the substrate which determines the specificity of the inhibition test; the determination of the enzyme activity is based on the spectrophotometric determination of glucose liberated by means of glucose dehydrogenase and nicotinamide-adenine dinucleotide as the cofactor.

A saccharase inhibitor unit (SIU) is defined as the inhibitory activity which reduces a given saccharolytic activity in a defined test batch by one unit (saccharase unit = SU); the saccharase unit is thereby defined as the enzyme activity which, under the given conditions, splits one μmol of sucrose per minute and thus leads to the liberation of one μmol each of glucose, which is determined in the test, and fructose, which is not recorded in the test.

The intestinal disaccharidase complex is obtained from swine small intestine mucosa by tryptic digestion, precipitation from 66% strength ethanol at −20° C., taking up of the precipitate in 100 mM phosphate buffer of pH 7.0 and finally dialysis against the same buffer.

100 μl of a dilution of the intestinal disaccharidase complex in 0.1 M maleate buffer of pH 6.25 are added to 10 μl of a sample solution which is made up such that the extinction of the test batch is at least 10%, but not more than 25%, below that of the 100% value, and the mixture is pre-incubated at 37° C. for 10 minutes. The dilution of the disaccharidase complex is to be adjusted to an activity of 0.1 SU/ml.

The saccharolytic reaction is then started by adding 100 μl of a 0.4 M solution of sucrose ("SERVA 35579") in 0.1 M maleate buffer of pH 6.25 and, after in incubation period of 20 minutes at 37° C., is stopped by adding 1 ml of glucose dehydrogenase reagent (1 small bottle of a lyophilised glucose dehydrogenase/mutarotase mixture ("MERCK 14053") and 331.7 mg of β-nicotinamide-adenine dinucleotide (free acid, "BOEHRINGER", degree of purity I) dissolved in 250 ml of 0.5 M tris buffer of pH 7.6). To determine the glucose, the mixture is incubated at 37° C. for 30 minutes and finally measured photometrically at 340 nm against a reagent blank (with the enzyme but without sucrose).

Calculation of the inhibitory activity of inhibitors is made difficult by the fact that even slight changes in the test system, for example a 100% value which varies slightly from determination to determination, have an influence on the test result which can no longer be ignored. These difficulties are by-passed by running a standard with each determination; a saccharase inhibitor of the formula $C_{25}H_{43}O_{18}N$ which has a specific inhibitory activity of 77,700 SIU/g and, when employed in the test in amounts of 10 to 20 ng, leads to an inhibition of the order of size specified above, is used as the standard. When the difference in the extinctions at 340 nm between the 100% value and the batch inhibited by the standard is known, it is possible to calculate the specific inhibitory activity of the inhibitor, expressed in saccharase inhibitor units per gram (SIU/g), in a known manner from the difference in extinction between the 100% value and the batch inhibited by the sample solution, taking into consideration the amount of inhibitor employed.

The following Examples illustrate processes for the production of compounds of the present invention.

EXAMPLE 1

N-Amino-1-desoxynojirimicin

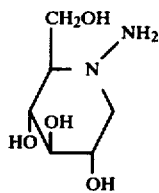

69 g of sodium nitrite are added in portions to 82 g of 1-desoxynojirimicin in 600 ml of 2 N HCl at 0° C. and the mixture is stirred at room temperature for 6 hours. It is then rendered alkaline with 1 l of concentrated ammonia solution, 166 g of zinc powder are added in portions, whilst cooling with ice, and the mixture is stirred overnight at room temperature and boiled under reflux for 3 hours. After cooling, the precipitate is filtered off, the volume is concentrated down to 200 ml in vacuo, the precipitate is filtered off and washed with water and the filtrate is boiled up with 800 ml of ethanol. Crude N-amino-1-desoxynojirimicin crystallises out of the solution, which has been filtered hot, and is recrystallised twice more from ethanol/water. Yield: 35 g, melting point: 186° to 189° C.

The mother liquors are collected and evaporated and the residue is chromatographed on 500 g of silica gel (particle size: 0.063 to 0.2 mm) with ethanol/water (10:2) as the running agent. A further yield of 27 g is obtained.

EXAMPLE 2

N-Amino-1,6-didesoxynojirimicin

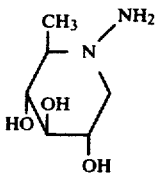

6.3 g of sodium nitrite in 30 ml of water are added dropwise to 4.5 g of 1,6-didesoxynojirimicin in 37 ml of 2 N Hcl at 0° C. and the mixture is stirred for 2 hours and left to stand in a refrigerator overnight. 180 ml of concentrated ammonia solution are then added, whilst cooling with ice, and 16 g of zinc powder are subsequently added to 0° to 20° C. The mixture is stirred at room temperature for 24 hours and boiled under reflux for 2 hours and, after cooling, the precipitate is filtered off and the filtrate is evaporated to dryness. The residue is taken up in a little 2 N HCl, the mixture is discharged onto a column containing a strongly acid ion exchanger and the column is rinsed with 2 l of water and eluted with 0.3 N ammonia solution. After evaporating the eluate, the residue is recrystallised from methanol. Yield: 1.3 g, melting point: 155° C.

The mother liquors are chromatographed on silica gel (particle size: 0.063 to 0.2 mm) with ethanol/water (10:2) as the running agent and give a further 1.4 g of the desired substance.

EXAMPLE 3

N-Benzylideneamino-1-desoxynojirimicin

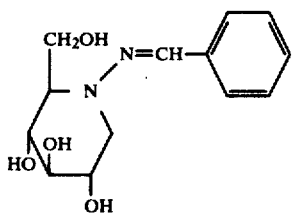

1 g of N-amino-1-desoxynojirimicin is dissolved in 5 ml of methanol and 5 ml of glacial acetic acid at 60° C., 1.1 ml of benzaldehyde are added and the mixture is left to stand at room temperature. After a short time, the reaction product precipitates in the crystalline form and is filtered off and recrystallised from methanol. 1.4 g of melting point 203° C. are obtained.

The compounds of Examples 4 to 16 are prepared analogously to these instructions. In the case of compounds which are not precipitated directly in the crystalline form, the reaction mixture is evaporated to dryness and the residue is recrystallised.

EXAMPLE 4

N-(2-Hydroxy-3-methoxybenzylidene)-amino-1-desoxynojirimicin

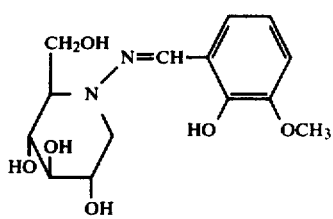

from N-amino-1-desoxynojirimicin and 2-hydroxy-3-methoxy-benzaldehyde, melting point: 239° C.

EXAMPLE 5

N-(3-Nitrobenzylidene)-amino-1-desoxynojirimicin

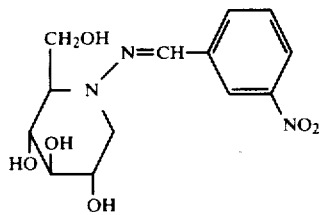

from N-amino-1-desoxynojirimicin and 3-nitrobenzaldehyde, melting point: 205° C.

EXAMPLE 6

N-(3-Phenylpropylidene)-amino-1-desoxynojirimicin

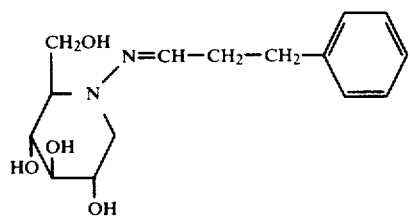

From N-amino-1-desoxynojirimicin and dihydrocinnamaldehyde, melting point: 156° C.

EXAMPLE 7

N-(4-Methylbenzylidene)-amino-1-desoxynojirimicin

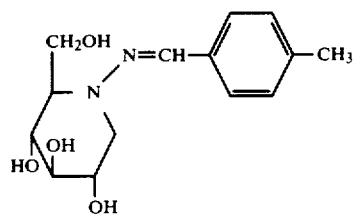

from N-amino-1-desoxynojirimicin and 4-methylbenzaldehyde, melting point: 209° C.

EXAMPLE 8

N-(4-Methoxybenzylidene)-amino-1-desoxynojirimicin

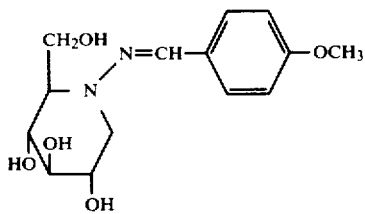

from N-amino-1-desoxynojirimicin and 4-methoxybenzaldehyde, melting point: 209° C.

EXAMPLE 9

N-(3-Cyclohexenyl)-methyleneamino-1-desoxynojirimicin

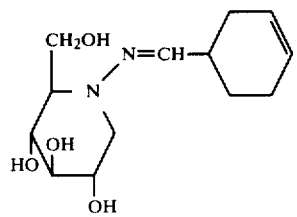

from N-amino-1-desoxynojirimicin and 3-cyclohexene-1-aldehyde, melting point: 143° C.

EXAMPLE 10

N-Undecylideneamino-1-desoxynojirimicin

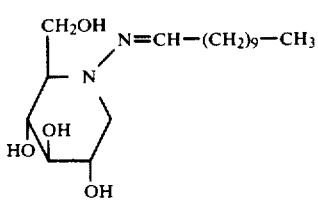

from N-amino-1-desoxynojirimicin and undecanal, melting point: 151° C.

EXAMPLE 11

N-Heptylideneamino-1-desoxynojirimicin

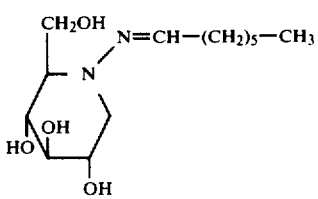

from N-amino-1-desoxynojirimicin and heptanal, melting point: 136° C.

EXAMPLE 12

1-Desoxy-N-furfurylideneaminonojirimicin

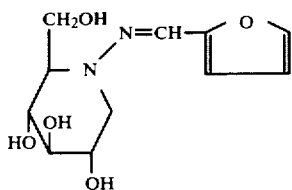

from N-amino-1-desoxynojirimicin and furfural, melting point: 151° to 152° C.

EXAMPLE 13

1-Desoxy-N-thenylideneaminonojirimicin

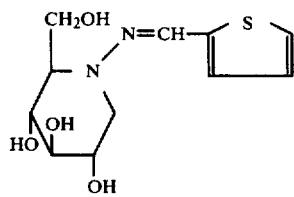

from N-amino-1-desoxynojirimicin and thiophene-2-aldehyde.

EXAMPLE 14

1-Desoxy-N-(3-pyridyl)-methyleneamino-nojirimicin

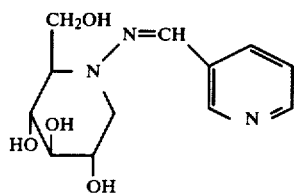

from N-amino-1-desoxynojirimicin and pyridine-3-aldehyde, melting point: 141° C.

EXAMPLE 15

N-(4-Chlorobenzylidene)-amino-1-desoxynojirimicin

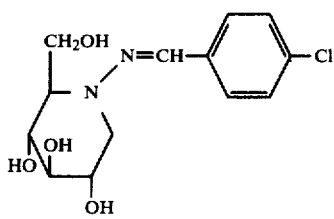

from N-amino-1-desoxynojirimicin and 4-chlorobenzaldehyde, melting point: 206° C.

EXAMPLE 16

N-(2-Methylmercaptobenzylidene)-amino-1-desoxynojirimicin

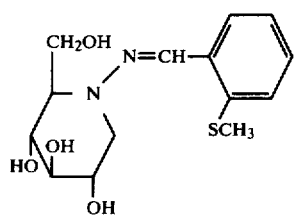

from N-amino-1-desoxynojirimicin and 2-methylmercaptobenzaldehyde, melting point: 178° C.

EXAMPLE 17

N-Benzylamino-1-desoxynojirimicin

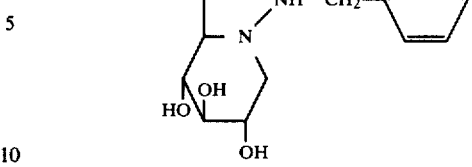

2 g of N-benzylideneamino-1-desoxynojirimicin, 30 ml of methanol, 0.5 g of NaBH$_3$CN and 1 ml of glacial acetic acid are stirred at room temperature overnight and the mixture is then boiled under reflux for one hour. The reaction mixture is evaporated in vacuo at a bath temperature of 40° C., the residue is taken up in 10 ml of 2 N HCl and the mixture is warmed on a waterbath until the evolution of H$_2$ has ended and is discharged onto a column which is 20 cm long and 2.5 cm in diameter and is filled with a cation exchanger (H+ form). After washing the column with 2 l of water, the reaction product is eluted with 0.3 N ammonia solution, the eluate is evaporated and the residue is recrystallised from methanol. 1.2 g of melting point 179° C. are obtained.

EXAMPLE 18

N-Acetamido-1-desoxynojirimicin

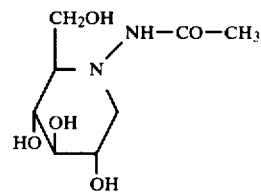

0.5 g of N-amino-1-desoxynojirimicin, 5 ml of water, a cation exchanger (amine form) and 0.5 ml of acetic anhydride are stirred vigorously for 30 minutes. The reaction mixture is then discharged onto a column which is 10 cm long and 1.5 cm in diameter and is filled with a strongly basic ion exchanger (OH— form) and the column is eluted with water until the pH of the eluate has reached 8. After elution, 200 mg of a hygroscopic foam of N-acetamido-1-desoxynojirimicin remain, which has the following characteristic spectroscopic data:

mass spectrum: m/e=220 (2%), 202 (15%), 189 (40%) and 147 (45%);

$^1$H-NMR (100 MHz, D$_2$O): δ=2.0 (s, CH$_3$-CO)

EXAMPLE 19

N-Heptylamino-1-desoxynojirimycin

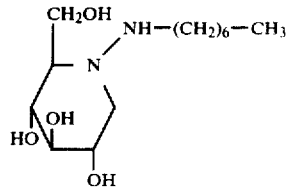

from 2 g N-Heptylideneamino-1-desoxynojirimycin analogously to Example 17; yield: 1.85 g Oil.

EXAMPLE 20

N-Dimethylamino-1-desoxynojirimycin

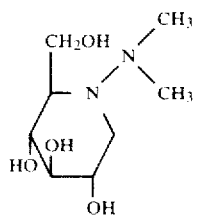

To a mixture of 2 g of N-amino-1-desoxynojirimycin, 5 ml of 30% strength fromaldehyde solution, 15 ml of methanol and 2 g of NaBH$_3$CN are added dropwise 1,5 ml glacial acetic acid. After stirring over night the solvent is stripped off in vacuo, the residue is dissolved in 2 N hydrochloric acid and the solution is discharged on to a column filled with an acidic cation exchanger.

After washing with water the reaction product is eluted with 0.3 N ammonia solution in methanol/water (10:1), the eluate is evaporated and the residue recrystallised from isopropanol/methanol. 1 g of melting point 177°–180° C. is obtained.

EXAMPLE 21

N-Dioctylamino-1-desoxynojirimycin

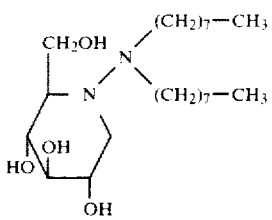

from 2 g of N-amino-1-desoxynojirimycin and octanal according to example 20; yield: 2.5 g, oil.

Among the new N-amino-3,4,5-trihydroxypiperidine salts of the invention, those salts that are pharmaceutically acceptable are particularly important and are preferred.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The new free N-amino-3,4,5-trihydroxypiperidines of the general formula I and their salts can be interconverted in any suitable manner; methods for such interconversion are known in the art.

The present invention also comprises pharmaceutically acceptable bioprecursors of the active compounds of the present invention.

For the purposes of this Specification the term pharmaceutically acceptable bioprecursor of an active compound of the invention means a compound having a structural formula different from the active compound but which nonetheless, upon administration to an animal or human being is converted in the patient's body to the active compound. What is claimed is:

1. A compound which is an N-amino-3,4,5-trihydroxypiperidine of the formula

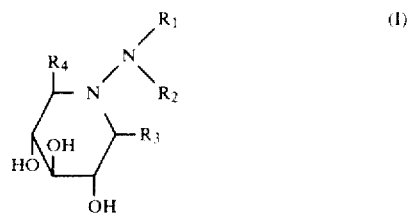

(I)

or a salt thereof,
in which

R$_1$ is a hydrogen atom, a formyl or carboxamido group, or a R$_5$, COR$_5$, CO$_2$R$_5$, CONHR$_5$, CONR$_5$R$_6$, CSR$_5$, CSNH$_2$, CSNHR$_5$, CSNR$_5$R$_6$, SO$_3$H or SO$_2$R$_5$ group, R$_2$ is a hydrogen atom or an R$_5$ group, or R$_1$ and R$_2$ together represent the grouping

R$_3$ denotes a hydrogen atom, a hydroxyl, mercapto, amine, cyano, carboxyl, carboxamido, aminomethyl, sulpho hydroxymethyl group or an OR$_5$, SR$_5$, NHR$_5$, NR$_5$R$_6$, CO$_2$R$_5$, CONHR$_5$, CONR$_5$R$_6$, CH$_2$NHR$_5$, CH$_2$NR$_5$R$_6$, CH$_2$NHR$_5$, CH$_2$NR$_5$COR$_6$, CH$_2$NHSO$_2$R$_5$, CH$_2$NR$_5$SO$_2$R$_6$, CH$_2$OR$_5$ or CH$_2$OCOR$_5$ group, R$_4$ denotes a hydrogen atom. a hydroxymethyl, formyl, carboxyl or carboxamido group or a R$_5$, CH$_2$OR$_5$, CHR$_5$OH, CHR$_5$OR$_6$, CR$_5$R$_6$OH, CR$_5$R$_6$OR$_7$, CR$_5$O, CO$_2$R$_5$, CONHR$_5$, CONR$_5$R$_6$ or CH$_2$X group wherein X is fluoro chloro, bromo, R$_5$, R$_6$ and R$_7$ independently of one another denote a straight-chain, branched or cyclic saturated or unsaturated aliphatic hydrocarbon group or an aromatic or a heterocyclic group derived from furane, pyrane, pyrrolidine, piperidine, pyrazole, imidazole, pyrimidine, pyridazine, pyrazine, triazine, pyrrole, pyridine, benzimidazole, quinoline, isoquinoline or purine, and $R_8$ and $R_9$ independently of each other denote a hydrogen atom or an $R_5$ group.

2. A compound according to claim 1, in which $R_3$ is a hydrogen atom or a hydroxyl, sulpho, cyano, amonomethyl, $C_1$ to $C_6$ alkylaminomethyl or ($C_1$ or $C_6$ alkyl)-carbonylaminomethyl group and $R_4$ is a hydroxymethyl, hydroxy-($C_1$ to $C_6$ alkyl)-methyl, $C_1$ to $C_7$ alkyl or $C_1$ or $C_5$ alkoxymethyl group.

3. A compound according to claim 1, of the formula

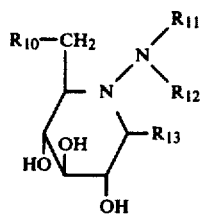

in which $R_{10}$ is a hydrogen atom or a hydroxyl or methoxy group, $R_{11}$ is a hydrogen atom or a $C_1$ to $C_4$ alkyl, $C_1$ to $C_4$ alkoxy, $C_1$ to $C_4$ alkylsulphonyl, $C_1$ to $C_4$ alkylcarbonyl or phenyl group, $R_{12}$ is a hydrogen atom, a $C_1$ to $C_{12}$ alkyl group which is optionally substituted by hydroxyl, $C_1$ to $C_4$ alkoxy, carboxyl, $C_5$ to $C_7$ cycloalkyl or phenylsulphonylamino, a $C_2$ to $C_4$ alkenyl group, a phenyl, phenyl-$C_1$ to $C_4$ alkyl or benzoylmethyl group which is optionally substituted in the phenyl ring by halogen, $C_1$ to $C_4$ alkyl, hydroxyl, di-$C_1$ to $C_4$ alkylamino or $C_1$ to $C_4$ alkoxy, or a $C_5$ to $C_7$ cycloalkyl, furylmethyl, pyridylmethyl or diphenylmethyl group and $R_{13}$ is a hydrogen atom or a ($C_1$ to $C_6$ alkyl)-carbonylaminomethyl, phenylcarbonylaminomethyl, phenylsulphonylaminomethyl, ($C_1$ to $C_4$ alkoxy)-carbonyl or ($C_1$ or $C_6$ alkyl)-aminocarbonyl group.

4. A compound according to claim 3, in which $R_{11}$ is a hydrogen atom or a methyl, ethyl, acetyl, methylsulphonyl, propionyl or phenyl group.

5. A compound according to claim 3 in which $R_{12}$ is a phenyl, phenyl-$C_1$ to $C_4$ alkyl or benzoylmethyl group substituted in the phenyl ring by fluorine or chlorine.

6. A compound according to claim 1 of the formula

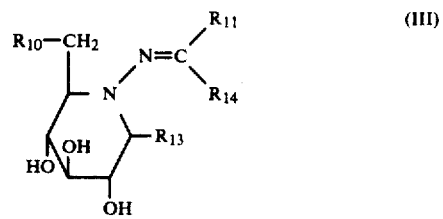

in which $R_{10}$ is a hydrogen atom or a hydroxy or mexthoxy group, $R_{11}$ is a hydrogen atom or a $C_1$ to $C_4$ alkyl, $C_1$ to $C_4$ alkoxy, $C_1$ to $C_4$ alkylsulphonyl, $C_1$ to $C_4$ alkylcarbonyl or phenyl group, $R_{13}$ is a hydrogen atom or a ($C_1$ to $C_6$ alkyl)-carbonylaminomethyl, phenylcarbonylaminomethyl, phenylsulphonylaminomethyl, ($C_1$ to $C_4$ alkoxy)-carbonyl or ($C_1$ or $C_6$ alkyl)-aminocarbonyl group, $R_{14}$ is a hydrogen atom, a $C_1$ to $C_{12}$ alkyl group which is optionally substituted by hydroxyl, $C_1$ to $C_4$ alkoxy or phenylsulphonylamino, a $C_5$ to $C_7$ cycloalkyl, $C_2$ to $C_{12}$ alkenyl or carboxyl group, a phenyl, phenyl-$C_1$ to $C_4$ alkyl or benzoyl group which is optionally substituted in the phenyl ring by halogen, $C_1$ to $C_4$ alkyl, hydroxyl, nitro, di-$C_1$ to $C_4$ alkylamino, $C_1$ to $C_4$ alkoxy or carboxyl, or a furyl or pyridyl group.

7. A compound according to claim 6 in which $R_{14}$ is a phenyl, phenyl-$C_1$ to $C_4$ alkyl or benzoylmethyl radical substituted in the phenyl ring by fluorine or chlorine.

8. A compound according to claim 1 which is N-(4-chlorobenzylidine)-amino-1-desoxynojirimicin.

9. A pharmaceutical composition containing as an active ingredient an antidiabetically effective amount of a compound according to claim 1 in admixture with a solid or liquefied gaseous diluent.

10. A composition according to claim 9 containing from 0.1 to 99.5% by weight of the said active ingredient.

11. A medicament in dosage unit form comprising an antidiabetically effective amount of a compound according to claim 1 together with an inert pharmaceutical carrier.

12. A medicament of claim 11 in the form of tablets, pills, dragees, capsules or ampoules.

13. A method of combating diabetes in warm-blooded animals which comprises administering to the animals an effective amount of an anti-diabetically active compound according to Claim 1 either alone or in admixture with a diluent or in the form of a medicament.

14. A method according to claim 13 in which the active comnpound is administered in an amount of 1 to $1 \times 10^4$ SIU per kg body weight per day.

15. A method according to claim 14 in which the active compound is administered orally.

* * * * *